United States Patent [19]  [11] 3,968,228
Hoff et al.  [45] July 6, 1976

[54] 4-NITRO-5-CYANOIMIDAZOLES AS COCCIDIOSTATS

[75] Inventors: Dale R. Hoff, Basking Ridge; Peter Kulsa, Plainfield; Helmut H. Mrozik, Matawan; Edward F. Rogers, Middletown, all of N.J.

[73] Assignee: Merck & Co., Inc., Rahway, N.J.

[22] Filed: Feb. 10, 1975

[21] Appl. No.: 548,655

Related U.S. Application Data

[60] Division of Ser. No. 415,480, Nov. 13, 1973, abandoned, which is a continuation of Ser. No. 177,470, Sept. 2, 1971, abandoned.

[52] U.S. Cl................................. 424/273; 424/248
[51] Int. Cl.². ....................................... A61K 31/415
[58] Field of Search............................ 424/248, 273

[56] References Cited
FOREIGN PATENTS OR APPLICATIONS
1,153,347  1/1966  United Kingdom Primary Examiner—V. D. Turner
Attorney, Agent, or Firm—Richard A. Thompson; J. Jerome Behan

[57] ABSTRACT

4-Nitro-5-cyanoimidazoles substituted with a 1-loweralkyl group and variously substituted at the 2-position are useful as antiparasitic agents particularly as coccidiostats. The 4-nitro-5-cyanoimidazole coccidiostats are included in compositions useful for administration to poultry as treatment for coccidiosis.

3 Claims, No Drawings

4-NITRO-5-CYANOIMIDAZOLES AS COCCIDIOSTATS

This is a division of application Ser. No. 415,480 filed Nov. 13, 1973 now abandoned which application is a continuation of application Ser. No. 177,470 filed Sept. 2, 1971, now abandoned.

SUMMARY OF THE INVENTION

This invention relates generally to new and useful compounds classed as 4-nitro-5-cyanoimidazoles and processes for their preparation. In addition, this invention relates to the prevention and treatment of coccidiosis in poultry. More particularly, it is concerned with the effectiveness of 4-nitro-5-cyanoimidazoles as coccidiostats and with compositions containing said compounds. It is therefore an object of this invention to provide new compounds which possess antiprotozoal and antibacterial activity. Another object is to provide specifically for compounds which are active against the particular protozoa which cause coccidiosis in poultry. Still another is to provide processes for the preparation of said compounds. Another object of this invention shall be the compositions containing said antiprotozoal compounds for administration to poultry infected with coccidiosis or for the prevention of coccidiosis in poultry. Further objects will become apparent on a further reading of the description.

DESCRIPTION OF THE INVENTION

The 4-nitro-5-cyanoimidazoles which have been found to be very active in treating and preventing coccidiosis in poultry are of the following structural formula:

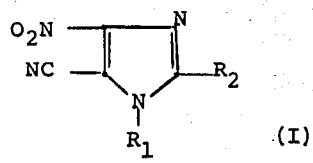

wherein $R_1$ is loweralkyl; $R_2$ is carbamoyl, mono- or di-N-loweralkylcarbamoyl, carboxy-alkalimetal salt, phenyl substituted with nitro, halo or mono- or di-N-loweralkylcarbamoyl; carboxaldehyde, carboxaldehyde-thiosemicarbazone carboxaldehyde-oxime, substituted methyl or 1-substituted ethyl wherein the substituents are hydroxy, halo, loweralkylsulfonyl, loweralkanoyloxy, halophenylthio, halophenylsulfoxide, 1-morpholino, trifluoromethylphenoxyanilino, phenoxycarbonyloxy, halobenzoyloxy, halophenoxy, carbamoyloxy, mono- or di-N-loweralkylcarbamoyloxy or N-loweralkanoylcarbamoyloxy.

In addition to the compounds of structural formula I, compounds of the formula:

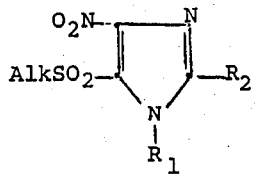

wherein $R_1$ and $R_2$ are as previously defined and Alk is loweralkyl, are novel compounds which are intermediates in the preparation of compounds of formula I, also possessing broad antibacterial activity. They are particularly active against Staphylococcus aureus, Escherichia coli, and Streptococcus pyogenes.

In describing this invention, the term "lower" when used in terms as "loweralkyl" or "loweralkoxy" means that the carbon chain contains from 1 to 5 carbon atoms in either a straight or branched configuration. The term "lower" when used in terms such as "loweralkanoyl", or "loweralkanoyloxy" means that the carbon chain contains from 2 to 5 carbon atoms in either a straight or branched configuration. The term "carbamoyl" defines the group

and the term "carbamoyloxy" defines the term

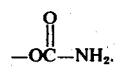

By "halogen" or "halo" is meant the halogen atoms fluorine, chlorine, bromine, and iodine.

DESCRIPTION OF THE PREFERRED EMBODIMENTS OF THE INVENTION

One aspect of the preferred embodiments of this invention is realized by the following structural formula:

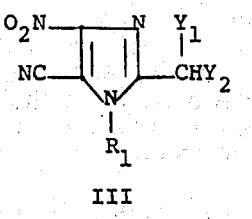

wherein $R_1$ is loweralkyl, $Y_1$ is hydrogen or methyl, and $Y_2$ is hydroxy, loweralkanoyloxy, carbamoyloxy, mono- or di-N-loweralkylcarbamoyloxy, phenoxycarbonyloxy, halobenzoyloxy, or halophenoxy.

Compounds exemplary of this embodiment of the invention are as follows:

1-methyl-2-hydroxymethyl-4-nitro-5-cyanoimidazole,
1-methyl-2-acetoxymethyl-4-nitro-5-cyanoimidazole,
1-methyl-2-propionyloxymethyl-4-nitro-5-cyanoimidazole,
1-methyl-2-phenoxycarbonyloxymethyl-4-nitro-5-cyanoimidazole,
1-methyl-2-(p-fluorobenzoyloxymethyl)-4-nitro-5-cyanoimidazole,
1-methyl-2-(p-bromobenzoyloxymethyl)-4-nitro-5-cyanoimidazole,
1-methyl-2-(o-chlorobenzoyloxymethyl)-4-nitro-5-cyanoimidazole,
1-methyl-2-(p-fluorophenoxymethyl)-4-nitro-5-cyanoimidazole,
1-methyl-2-(o-bromophenoxymethyl)-4-nitro-5-cyanoimidazole,
1-methyl-2-(1-hydroxyethyl)-4-nitro-5-cyanoimidazole, 1-methyl-2-(1-acetoxyethyl)-4-nitro-5-cyanoimidazole,
1-methyl-2-carbamoyloxymethyl-4-nitro-5-cyanoimidazole,
1-methyl-2-carbamoyloxymethyl-4-nitro-5-cyanoimidazole,
1-methyl-2-(N-methylcarbamoyloxymethyl)-4-nitro-5-cyanoimidazole,
1-methyl-2-(N,N-diethylcarbamoyloxymethyl)-4-nitro-5-cyanoimidazole,
1-methyl-2-(1-carbamoyloxyethyl)-4-nitro-5-cyanoimidazole,
1-ethyl-2-acetoxymethyl-4-nitro-5-cyanoimidazole,
1-ethyl-2-propionyloxymethyl-4-nitro-5-cyanoimidazole, and
1-ethyl-2-(1-hydroxyethyl)-4-nitro-5-cyanoimidazole.

Another aspect of the preferred embodiments of this invention is realized by the following structural formula:

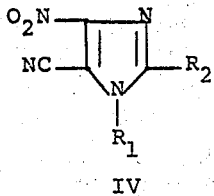

IV wherein $R_1$ is loweralkyl and $R_2$ is carbamoyl, phenyl substituted with nitro, halo, or mono- or di-N-loweralkylcarbamoyl, loweralkylsulfonylloweralkyl, carboxaldehyde, carboxaldehyde-thiosemicarbazone, carboxaldehydeoxime, carboxyalkali metal salt, and substituted loweralkyl wherein the substituents are halo 1-morpholino, halophenylthio or halophenylsulfoxide.

Compounds exemplary of this embodiment of the invention are as follows:

1-methyl-2-carbamoyl-4-nitro-5-cyanoimidazole,
1-methyl-2-(p-nitrophenyl)-4-nitro-5-cyanoimidazole,
1-methyl-2-(o-nitrophenyl)-4-nitro-5-cyanoimidazole,
1-methyl-2-(o-nitrophenyl)-4-nitro-5-cyanoimidazole,
1-methyl-2-(p-fluorophenyl)-4-nitro-5-cyanoimidazole,
1-methyl-2-(m-chlorophenyl)-4-nitro-5-cyanoimidazole,
1-methyl-2-(o-bromophenyl)-4-nitro-5-cyanoimidazole,
1-methyl-2-(p-carbamoylphenyl)-4-nitro-5-cyanoimidazole,
1-methyl-2-[p-(N-methylcarbamoyl)-phenyl]-4-nitro-5-cyanoimidazole,
1-methyl-2-[p-(N,N-diethylcarbamoyl)-phenyl]-4-nitro-5-cyanoimidazole,
1-methyl-2-(o-carbamoylphenyl)-4-nitro-5-cyanoimidazole,
1-methyl-2-methylsulfonylmethyl-4-nitro-5-cyanoimidazole,
1-methyl-2-ethylsulfonylethyl-4-nitro-5-cyanoimidazole,
1-ethyl-2-ethylsulfonylethyl-4-nitro-5-cyanoimidazole,
1-ethyl-2-carbamoyl-4-nitro-5-cyanoimidazole,
1-ethyl-2-chloromethyl-4-nitro-5-cyanoimidazole, and
1-ethyl-2-bromoethyl-4-nitro-5-cyanoimidazole.

Coccidiosis is a common and widespread poultry disease caused by several species of protozoan parasites of the genus Eimeria, such as *E. tenella, E. necatrix, E. acervulina, E. maxima, E. hagani* and *E. brunetti. E. tenella* is the causative agent of a severe and often fatal infection of the caeca of chickens, which is manifested by severe and extensive hemorrhage, accumulation of blood in the caeca, and the passage of blood in the droppings. *E. necatrix* attacks the small intestine of the chick causing what is known as intestinal coccidiosis. Related species of coccidia such as *E. meleagridis* and *E. Adenoides* are causitive organisms of coccidiosis in turkeys. When left untreated, the severe forms of coccidiosis lead to poor weight gain, reduced effeciency and high mortality in fowl. The elimination or control of this disease is, therefore, of paramount importance to the poultry raising industry.

Another preferred embodiment of this invention are the compositions containing the above 4-nitro-5-cyanoimidazoles which may be successfully employed to cure and prevent the development of coccidiosis when administered to poultry. The active compounds are conveniently fed to poultry as a component of the feed of the animals although it may be given dissolved or suspended in the drinking water. According to a preferred aspect of the invention, novel compositions for the treatment of coccidiosis are provided which comprise one or more 4-nitro-5-cyanoimidazoles intimately dispersed in or intimately admixed with an inert edible carrier or diluent. By an inert edible carrier or diluent is meant one that is nonreactive with respect to the imidazole, and that may be administered with safety to the animals to be treated. The carrier or diluent is preferably one that is or may be an ingredient of the animal feed.

The compositions which are a preferred feature of this invention are the so-called feed supplements in which the 4-nitro-5-cyanoimidazole is present in relatively large amounts and which are suitable for addition to the poultry feed either directly or after an intermediate dilution or blending step. Examples of carriers or diluents suitable for such compositions are animal feed ingredients such as distillers' dried grains, corn meal, citrus meal, fermentation residues, ground oyster shells, Attapulgus clay, wheat shorts, molasses solubles, corn cob meal, edible vegetable substances, toasted dehulled soya flour, soybean mill feed, antibiotic mycelia, soya grits, crushed limestone, and the like. The imidazole compound is intimately dispersed or admixed throughout the solid inert carrier by methods such as grinding, stirring, milling or tumbling. By selecting proper diluents and by altering the ratio of carrier to active ingredient, compositions of any desired concentration may be prepared. Formulations containing from about 1% to about 40% by weight and preferably from about 2–25% by weight, of the 4-nitro-5-cyanoimidazoles are particularly suitable for addition to poultry feedstuffs; those having from about 5–20% by weight of coccidiostat are very satisfactory. The active compound is usually dispersed or mixed uniformly in the diluent but in some instances may be absorbed on the carrier. Since it is convenient for the feed manufacturer to use about one pound of feed supplement for each ton of finished feed, the preferred concentration in the supplement is usually a function of the level of active ingredient desired in the finished feed.

Very low levels of 4-nitro-5-cyano-imidazoles in an animal feed are sufficient to afford the poultry good protection against coccidiosis. Preferably the compound is administered to chickens in an amount equal to about 0.00025% to 0.05% by weight of the daily feed intake. Optimum results are obtained by feeding at a level of about 0.001% to 0.01% by weight of the finished feed. For therapeutic treatment of an established coccidial infection, higher amounts of 4-nitro-5-cyano-imidazoles, i.e., up to about 0.1% by weight of the feed consumed, may be employed. The most advantageous dosage level will, of course, vary somewhat with particular circumstances such as the type and severity of the coccidial infection to be treated.

For treating poultry, the feed supplement is uniformly dispersed in the animal feed by suitable mixing or blending procedures.

Usually the feed supplements are further diluted with materials such as corn meal or soybean meal before being incorporated in the animal feed. In this intermediate processing step the level of the 4-nitro-5-cyanoimidazole in the carrier is brought down to about 0.1% to 1.0% by weight. This dilution serves to facilitate uniform distribution of the coccidiostat in the finished feed. The finished feed is one that contains a source of fat, protein, carbohydrate, minerals, vitamins and other nutritional factors.

In the above discussion of this invention, emphasis has been placed on solid compositions wherein the active ingredient is mixed with an edible carrier in a feed supplement, in a so-called premix or in the final poultry feedstuff. This is the preferred method of administering the imidazole of this invention. An alternate method of treatment is to dissolve or suspend the imidazole compound in the drinking water of the animals. The quantity of coccidiostat which may be administered in this fashion is, of course, limited by the solubility of the product in water of by the quantity that may be suspended in the water without undue settling. Emulsifiers or surface active agents may be employed for this latter purpose.

This invention is not limited to coccidiostatic compositions having 4-nitro-5-cyanoimidazole type compounds as the sole active ingredient. Also contemplated within its scope is what might be called "combined treatment" where a 4-nitro-5-cyanoimidazole and one or more other coccidiostats are administered concurrently. For such purposes, compositions may be prepared containing this imidazole compound admixed with one or more other coccidiostats such as sulfaquinoxaline, other sulfa compounds, 4,4'-dinitrocarbanilide-2-hydroxy-4,7-dimethylpyrimidine complex, 3,'-dinitrodiphenyldisulfide, 5-nitrofurfural semicarbazone, amprolium, zoalene, buquinolate, ethopabate, and the like.

It will likewise be understood by those skilled in this art that special feed supplement formulations and finished animal feeds containing vitamins, antibiotics, growth-promoting agents and other nutritional substances may include the imidazole compound of this invention. A typical product of this type is the following:

| Ingredient | Amount/lb. of Supplement, grams | |
|---|---|---|
| Riboflavin | 0.64 | |
| DL-calcium pantothenate | 2.10 | |
| Niacin | 3.67 | |
| Choline chloride | 50.00 | |
| Vitamin $B_{12}$ concentrate | 1.30 | mg. |
| Procaine penicillin | 0.84 | |
| Vitamin A (100,000 u./g.) | 3.38 | |
| Vitamin $D_3$ (200,000 u./g.) | 0.68 | |
| Arsanilic acid | 18.36 | |
| Butylated hydroxy toluene | 23.15 | |
| DL-methionine | 23.15 | |
| 1-methyl-2-acetoxymethyl-4-nitro-5-cyanoimidazole | 23.00 | |
| Distillers' grain to 1 pound | | |

Animal feed supplements having the following compositions are prepared by intimately mixing 1-methyl-4-nitro-5-cyanoimidazole and the particular edible solid diluent or diluents:

| | | lbs. |
|---|---|---|
| A. | 1-methyl-2-hydroxymethyl-4-nitro-5-cyanoimidazole | 7.5 |
| | Distillers' dried grains | 92.5 |
| B. | 1-methyl-2-ethylsulfonylethyl-4-nitro-5-cyanoimidazole | 5.0 |
| | Soybean mill feed | 50.0 |
| | Fine soya grits | 45.0 |
| C. | 1-ethyl-2-ethylsulfonylethyl-4-nitro-5-cyanoimidazole | 10.0 |
| | Molasses solubles | 90.0 |
| D. | 1-methyl-2-carbamoyloxymethyl-4-nitro-5-cyanoimidazole | 15.0 |
| | Corn distillers' grains | 55.0 |
| | Corn germ meal | 30.0 |
| E. | 1-methyl-2-hydroxymethyl-4-nitro-5-cyanoimidazole | 20.0 |
| | Wheat shorts | 30.0 |
| | Distillers' dried grains | 50.0 |
| F. | 1-methyl-2-acetoxymethyl-4-nitro-5-cyanoimidazole | 25.0 |
| | Corn distillers' dried grains | 75.0 |
| G. | 1-methyl-2-acetoxymethyl-4-nitro-5-cyanoimidazole | 40.0 |
| | Corn meal | 60.0 |
| H. | 1-methyl-2-hydroxymethyl-4-nitro-5-cyanoimidazole | 10.0 |
| | Nicarbazin | 15.0 |
| | Corn distillers' dired grains | 75.00 |

These supplements are made by mechanical milling or mixing of the ingredients to insure uniform distribution of the active compound.

The compounds of this invention which are active antiprotozoal agents and are employed in the above anticoccidial compositions are prepared by a variety of synthetic organic chemical processes. The particular synthetic step and the particular order of a series of synthetic steps is determined by the substituent groups present on the desired final molecule and the sensitivity of those substituents to side reactions.

The 5-cyano group is introduced into the imidazole nucleus by the method outlined in the following reaction scheme:

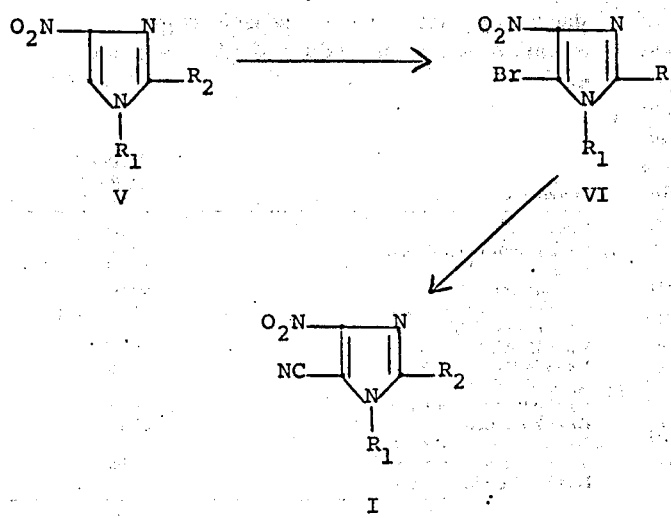

wherein $R_1$ and $R_2$ are as previously defined. In the above reaction scheme a substituted 4-nitroimidazole (V) is treated with a brominating agent such as liquid bromine, in nonreactive solvents usch as a lowercarboxylic acid, acetic acid being preferred, at a temperature of from 10° to 50°C., room temperature being preferred. The bromo compound (VI) is then treated with a metallic cyano compound in an inert solvent at a temperature of from 75° to 200°C. for a duration of from 1 to 24 hours. The metallic ions generally preferred are alkali metals, alkaline earth metals, and copper. Copper in its univalent form is preferred.

An alternative reaction scheme for the preparation of 5-cyano compounds is outlined in the following reaction scheme:

chloride, and the like at a temperature of from 10°C. to the reflux temperatures of the solvent employed. The sulfone (VIII) is then treated with a metallic cyanide preferably an alkalimetal, alkaline earth metal, or copper cyanide at a temperature of from 0° to 150°C. for a duration of from 3 minutes to 12 hours.

The above reactions whereby a cyano group is substituted in place of a bromo or methyl sulfonyl group are general ones and in place of the bromo or methyl sulfonyl groups there may be employed any leaving group susceptible to displacement by a nucleophilic reagent. Suitable groups are other halogens, as chloro or iodo, p-toluenesulfonyl, and the like. The reaction is run within any of the temperature and reaction times listed above depending on the relative reactivity of the displacing and leaving groups.

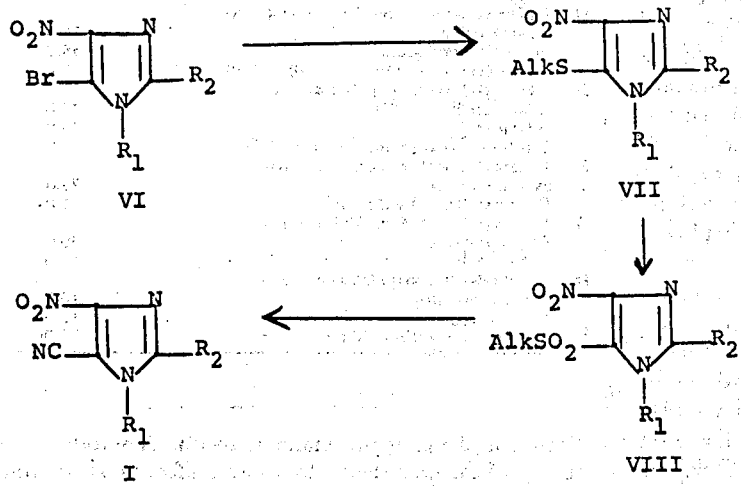

wherein $R_1$ and $R_2$ are as previously defined and Alk is loweralkyl. In the above reaction scheme the bromo compound (VI) is treated with an alkali metal salt of a loweralkyl mercaptan in a solvent such as loweralkanol, at a temperature of from room temperature to the reflux temperature of the solvent. The alkali metal salt of the loweralkyl mercaptan is prepared in advance of the reaction with the bromo compound using an alkali metal loweralkoxide in loweralkanol and a loweralkyl mercaptan. The alkali metal salt of the loweralkyl mercaptan is not isolated but rather used in solution as it is formed. The thus formed loweralkyl sulfide (VII) is oxidized to the sulfone (VIII) using oxidizing agents such as metachloroperbenzoic acid, hydrogen peroxide, and the like. The reaction is run in an inert solvent such as benzene, toluene, chloroform, carbon tetra- In the above reaction schemes care must be taken to insure that the particular reaction being employed does not interfere with any of the other substituents on the molecule. If necessary, sensitive groups can be protected to render them inert to the particular reaction, with the protecting group being subsequently removed. Alternatively, the order of a series of reactions can be modified such that sensitive groups encompassed in the definition of $R_1$ and $R_2$ are substituted on the molecule subsequent to the above reaction schemes. This technique is possible because the order of the substitution of the cyano group on the 5-position of the imidazole nucleus and the substitution of $R_1$ and $R_2$ on the 1- and 2-positions of the imidazole nucleus is not critical. The group most sensitive to side reactions is the hydroxy group which is sensitive to bromination, oxidation and other reactions. Where the reactions preparative of the cyano group do not interfere with the reactions preparative of the $R_1$ and $R_2$ groups, the order of reaction is determined only by questions of practicality.

Variations of the substituents at the 2-position are usually effected by starting with the readily available hydroxyloweralkyl group, particularly the hydroxymethyl and the 1-hydroxyethyl groups. By reacting the hydroxy group with a halocarboxyl derivative such as loweralkanoyl halides, halobenzoylhalides, phenoxycarbonylhalides, phosgene or mono- or di-N-loweralkyl carbamoylhalides, the hydrogen atom of the hydroxy group is displaced, the oxygen atom is bonded to the carbonyl group and the halide is displaced to bond with the hydrogen atom forming compounds with the carbonyloxy connecting group

in common. The carbonyloxy group is substituted on the carbonyl with loweralkyl, halophenyl, phenoxy, chloro, or mono- or di-loweralkylamino.

The hydroxyl group can be reacted with a halogenating agent such as thionylchloride, thionylbromide, phosphorous tribromide, phosphorous oxychloride and the like to produce the haloloweralkyl compound. The reaction is run in an inert solvent such as benzene, or toluene at a temperature of from room temperature to the reflux temperature of the reaction mixture. The reaction is generally complete in from 10 minutes to 4 hours at the reflux temperature of the reaction mixture.

The halo compound may in turn be displaced by alkali metal salts of alcohols of both the aliphatic and aromatic varieties. The sodium salt is prepared and reacted with the halo compound as discussed hereinabove. The reaction works equally well with loweralkanols, loweralkylmercaptans, phenols, halophenols, and thiophenols. The thio compounds can be oxidized using oxidizing agents such as hydrogen peroxide and metachloroperbenzoic acid. By stoichiometric control of the amounts of the oxidizing agents the sulfoxide and the sulfone can be independently prepared.

In addition, the hydroxy group can be oxidized selectively to the carboxylic acid or the aldehyde. Potassium permanganate is employed to oxidize the alcohol to the carboxylic acid. Usually water is employed to dissolve the potassium permanganate and an organic solvent such as acetone, chloroform, and the like to dissolve the imidazole. The reaction is generally complete in from 1 to 10 hours at a temperature of from 20°–50°C. Initially the reaction is cooled to from 0° to 10°C. to prevent an initial exothermic reaction. The carboxylic acid is usually isolated as the potassium salt thereof.

Using lead tetraacetate in an inert solvent as benzene, toluene, chloroform, and the like, the alcohol can be selectively oxidized to the carboxaldehyde. The reaction is run at a temperature of from room temperature to the reflux temperature of the solvent employed for from 1 to 24 hours. The reaction is generally complete in from 3 to 8 hours at 80°C. The aldehyde serves as an intermediate for the oxime and thiosemicarbazone derivatives which are prepared by procedures which are well known to those skilled in the art.

The following examples are presented in order that the invention might be more fully understood. However, owing to the numerous possible combinations of reactions and reaction sequences, the examples presented infra are to be construed as being exemplary of one particular mode of performing the invention, and not a limitation upon other modes.

EXAMPLE 1

A. 1-Methyl-2-acetoxymethyl-4-nitroimidazole 0.828 G. (0.004 moles) of 1-methyl-2-hydroxymethyl-4-nitroimidazole is dissolved in 10 ml. of acetic acid and treated with 0.460 g. (a 10% excess, 0.004 moles) of acetic anhydride and refluxed for 4 hours. The reaction mixture is cooled and 15 ml. of water is added and extracted with methylene chloride. The extracts are washed with aqueous sodium carbonate, dried and evaporated to dryness affording 0.760 g. of 1-methyl-2-acetoxymethyl-4-nitroimidazole, m.p. 93° to 95°C.

B.

1-Methyl-2-acetoxymethyl-4-nitro-5-bromoimidazole 1.99 G. (0.01 moles) of 1-methyl-2-acetoxymethyl-4-nitroimidazole is dissolved in 20 ml. of acetic acid and treated with 0.9 g. (0.011 moles) of sodium acetate and 1.60 g. (0.01 moles) of bromine and heated at 100°C. for 24 hours. Additional quantities of sodium acetate (0.011 moles) and bromine 1.6 g. (0.01 moles) are added and the heating continued for 18 hours. The reaction mixture is cooled, 30 ml. of water is added and extracted with methylene chloride. The methylene chloride extracts are washed with aqueous sodium carbonate, dried and evaporated to dryness affording 1.5 g. of 1-methyl-2-acetoxymethyl-4-nitro-5-bromoimidazole, m.p. 92° to 97°C.

When in the above procedure the following compounds are brominated the listed products are obtained:

EXAMPLE 1-B

| Quantity | Starting Material | Reaction Condition | Product | m.p. |
| --- | --- | --- | --- | --- |
| 17.4 g. (0.066 m.) | 1-methyl-2-(p-nitrophenyl)-4-nitroimidazole | 12 hr. (100°C.) | 1-methyl-2-(p-nitrophenyl)-4-nitro-5-bromoimidazole | 185–188°C. |
| 1.105 g. (0.005 m.) | 1-methyl-2-(p-fluorophenyl)-4-nitroimidazole | 4 hr. (100°C.) | 1-methyl-2-(p-fluorophenyl)-4-nitro-5-bromoimidazole | 146–147°C. |
| 8.22 g. (0.03 m.) | 1-methyl-2-[p-(N,N-dimethylcarbamoyl)-phenyl]-4-nitroimidazole | 12 hr. (100°C.) | 1-methyl-2-[p-(N,N-dimethylcarbamoyl-phenyl]-4-nitro-5-bromoimidazole | 212–216°C. |

C.

1-Methyl-2-acetoxymethyl-4-nitro-5-cyanoimidazole 2.78 G. (0.01 moles) of 1-methyl-2-acetoxymethyl-4-nitro-5-bromoimidazole and 0.0115 moles of cupric cyanide are combined in 20 ml. of dimethylformamide and heated on a steam bath for 12 hours. The reaction mixture is cooled and poured into 200 ml. of 3% aqueous ammonia and extracted with chloroform. The extracts are washed with water, dried and evaporated under a high vacuum. The residue is recrystallized from isopropanol affording 1.0 g. 1-methyl-2-acetoxymethyl-4-nitro-5-cyanoimidazole, m.p. 92° to 93°C.

When in the above procedure the following compounds are treated with a 20% molar excess of cupric cyanide the following products are obtained:

EXAMPLE 1-C

| Quantity | Starting Material | Reaction Condition | Product | m.p. |
|---|---|---|---|---|
| 6.54 g. (0.02 m.) | 1-methyl-2-(p-nitrophenyl)-4-nitro-5-bromoimidazole | 18 hrs. (100°C.) | 1-methyl-2-(p-nitrophenyl)-4-nitro-5-cyanoimidazole | 184–188°C. |
| 3.00 g. (0.01 m.) | 1-methyl-2-(p-fluorophenyl)-4-nitro-5-bromoimidazole | 18 hrs. (100°C.) | 1-methyl-2-(p-fluorophenyl)-4-nitro-5-cyanoimidazole | 140–143°C. |
| 3.53 g. 0.01 m.) | 1-methyl-2-[p-(N,N-dimethylcarbamoyl)-phenyl]-4-nitro-5-bromoimidazole | 16 hrs. (100°C.) | 1-methyl-2-[p-(N,N-dimethylcarbamoyl)-phenyl]-4-nitro-5-cyanoimidazole | 151–155°C. |

EXAMPLE 2

1-Methyl-2-hydroxymethyl-4-nitro-5-cyanoimidazole 2.0 G. of 1-methyl-2-acetoxymethyl-4-nitro-5-cyanoimidazole is dissolved in 100 ml. of anhydrous methanol which is saturated with anhydrous gaseous ammonia at 0°C. The reaction mixture is stirred for 15 minutes at 0°C. and the methanol and ammonia removed under high vaccum. The residue is recrystallized from isopropanol affording 1.2 g. of 1-methyl-2-hydroxymethyl-4-nitro-5-cyanoimidazole, m.p. 122° to 124°C.

EXAMPLE 3

1-Methyl-2-bromoethyl-4-nitro-5-bromoimidazole 0.596 G. (0.00214 moles) of 1-methyl-2-acetoxymethyl-4-nitro-5-bromoimidazole is dissolved in 20 ml. of acetic acid and treated with gaseous HBr for 5 minutes at room temperature. The reaction mixture is refluxed on a steam bath for 1 hour, cooled and evaporated to dryness. The residue is dissolved in chloroform, treated with 10% potassium bicarbonate solution. The chloroform layer is separated, dried and evaporated to dryness, affording 0.568 g. of 1-methyl-2-bromomethyl-4-nitro-5-bromoimidazole, recovered as an oil.

EXAMPLE 4

A.

1-Methyl-2-hydroxymethyl-4-nitro-5-thiomethylimidazole

A 10 ml. solution of sodium methoxide in methanol is treated with excess methyl mercaptan affording the sodium salt of methyl mercaptan which is used in solution. 0.944 G. (0.004 moles) of 1-methyl-2-hydroxymethyl-4-nitro-5-bromoimidazole is dissolved in 10 ml. of methanol and treated with the previously prepared methanol solution of the sodium salt of methyl mercaptan and refluxed for 2 hours. The reaction mixture is cooled, evaporated to dryness and the residue treated with 10 ml. of water. The suspension is filtered and washed with water affording 0.35 g. of 1-methyl-2-hydroxymethyl-4-nitro-5-thiomethylimidazole, m.p. 140° to 141°C.

When 1.05 g. (0.0035 moles) of 1-methyl-2-bromomethyl-4-nitro-5-bromoimidazole and 38 ml. of 2.5 N sodium thiomethylate is employed in the above procedure, there is obtained 0.58 g. of 1-methyl-2-methylthiomethyl-4-nitro-5-thiomethylimidazole, m.p. 85°–90°C.

B.

1-Methyl-2-hydroxymethyl-4-nitro-5-methylsulfonylimidazole 0.59 G. (0.0029 moles) of 1-methyl-2-hydroxymethyl-4-nitro-5-thiomethylimidazole is dissolved in 15 ml. of chloroform and combined with 1.18 g. (0.0058 moles) of m-chloroperbenzoic acid dissolved in 10 ml. of chloroform and refluxed for 3 days. The reaction mixture is filtered, the solid material washed with chloroform and dried to 0.53 g. of 1-methyl-2-hydroxymethyl-4-nitro-5-methylsulfonylimidazole, m.p. 182° to 185°C.C.

When 0.92 g. (0.004 moles of 1-methyl-1-methylthiomethyl-4-nitro-5-thiomethylimidazole is oxidized with 3.25 g. (0.016 moles) of m-chloroperbenzoic acid as in the above procedure, there is obtained 1-methyl-2-methylsulfonylmethyl-4-nitro-5-methylsulfonylimidazole, m.p. 184° to 185°C.

C.

1-Methyl-2-hydroxymethyl-4-nitro-5-cyanoimidazole 2.21 G. (0.01 moles) of 1-methyl-2-hydroxymethyl-4-nitro-5-methylsulfonylimidazole and 0.715 g. of potassium cyanide in 20 ml. of dry dimethylsulfoxide are heated at 100°C. for 30 minutes. The reaction mixture is diluted with an equal volume of water and extracted with ethyl acetate. The combined extracts are dried and evaporated to dryness affording an oily residue which is recrystallized from isopropanol affording 1-methyl-2-hydroxymethyl-4-nitro-5-cyanoimidazole, m.p. 122° to 124°C.

When 0.297 g. (0.001 moles) of 1-methyl-2-methylsulfonylmethyl-4-nitro-5-methylsulfonylimidazole is treated with 0.078 g. of potassium cyanide as in the above procedure there is obtained 1-methyl-2-methylsulfonylmethyl-4-nitro-4-cyanoimidazole, m.p. 185° to 195°C.

EXAMPLE 5

1-Methyl-2-chloromethyl-4-nitro-5-cyanoimidazole 1.6 G. of 1-methyl-2-hydroxymethyl-4-nitro-5-cyanoimidazole is dissolved in 25 ml. of benzene and treated with 2.7 ml. of thionyl chloride. The reaction mixture is refluxed for 1 hour, cooled, filtered and evaporated to dryness. The residue is recrystallized from isopropanol affording 0.6 g. of 1-methyl-2-chloromethyl-4-nitro-5-cyanoimidazole.

EXAMPLE 6

1-Methyl-2-(p-chlorophenoxymethyl)-4-nitro-5-cyanoimidazole 0.98 G. (0.004 moles of 1-methyl-2-bromomethyl-4-nitro-5-cyanoimidazole is dissolved in 15 ml. of tetrahydrofuran, cooled to 0°C. and added to a previously prepared solution of 0.61 g. of the sodium salt of p-chlorophenol in 10 ml. of tetrahydrofuran. The reaction mixture is stirred for 3 hours at 0°C. After the addition is complete, 3 drops of acetic acid is added to the reaction mixture and the reaction mixture is evaporated to dryness. The residue is dissolved in methylene chloride and washed with a 2.5 N solution of sodium hydroxide. The methylene chloride solution is dried, evaporated to dryness, and the residue triturated with ether affording 750 mg. of 1-methyl-2-(p-chlorophenoxymethyl)-4-nitro-5-cyanoimidazole, m.p. 128° to 132°C.

When the above procedure is carried out utilizing 4-(m-trifluoromethylphenoxy)-aniline in place of the sodium salt of p-chlorophenol and without the acetic acid addition, there is obtained 1-methyl-2-[4-(m-trifluoromethylphenoxy)-anilinomethyl]-4-nitro-5-cyanoimidazole, m.p. 124° to 126°C.

When morpholine is employed in place of 4-(m-trifluoromethylphenoxy)-aniline there is obtained 1-methyl-2-morpholinomethyl-4-nitro-5-cyanoimidazole, m.p. 112° to 115°C.

EXAMPLE 7

1-Methyl-2-ethylsulfonylmethyl-4-nitro-5-cyanoimidazole

A.

1-methyl-2-ethylthiomethyl-4-nitro-5-cyanoimidazole 2.45 G. (0.01 moles) of 1-methyl-2-bromomethyl-4-nitro-5-cyanoimidazole is dissolved in 20 ml. of tetrahydrofuran at −15°C. and treated dropwise with a tetrahydrofuran solution of the sodium salt of ethyl mercaptan. The reaction mixture is stirred for ½ hour at −15°C. and treated with 0.5 g. of acetic acid. The reaction mixture is evaporated to dryness and the residue chromatographed on silica gel G eluting with chloroform followed by a methanol/chloroform mixture affording 1.3 g. of 1-methyl-2-ethylthiomethyl-4-nitro-5-cyanoimidazole, which is an oil and is used as is in the subsequent step.

B.

1-Methyl-2-ethylsulfonylmethyl-4-nitro-4-cyanoimidazole

The above 1-methyl-2-ethylthiomethyl-4-nitro-5-cyanoimidazole is dissolved in 20 ml. of methylene chloride and treated with 2 g. of m-chloroperbenzoic acid with stirring for 15 hours at room temperature. The reaction mixture is refluxed for 3 hours, cooled, diluted with methylene chloride and treated with a large excess of an aqueous solution of sodium carbonate. The methylene chloride solution is evaporated to dryness and the residue recrystallized from dimethylformamide/isopropanol, affording 750 mg. of 1-methyl-2-ethylsulfonylmethyl-4-nitro-5-cyanoimidazole, m.p. 126° to 128°C.

When 0.408 g. (0.00126 moles) of 1-methyl-2-[1-(p-chlorophenylthio)-ethyl]-4-nitro-5-cyanoimidazole is oxidized with 0.256 g. (0.00126 moles) of m-chloroperbenzoic acid according to the above procedure, there is obtained 0.31 g. of 1-methyl-2-[1-(p-chlorophenylsulfinyl)-ethyl]-4-nitro-5-cyanoimidazole, m.p. 150° to 160°C.

EXAMPLE 8

1-Methyl-2-carbamoyloxymethyl-4-nitro-5-cyanoimidazole

A solution of 0.182 g. (0.001 moles) of 1-methyl-2-hydroxymethyl-4-nitro-5-cyanoimidazole in 20 ml. of methylene chloride is treated with chlorosulfonylisocyanate (0.0012 moles). The reaction mixture is allowed to stand at room temperature for 3 hours. The solvent is removed in vacuo and the residue dissolved in 2 ml. of water and heated at 50°C. for 1 hour. The aqueous suspension is cooled and filtered and the solid material recrystallized from dimethylformamide/methanol affording pure 1-methyl-2-carbamoyloxymethyl-4-nitro-5-cyanoimidazole, m.p. 225° to 228°C.

When 0.741 g. (0.013 moles) of methylisocyanate is reacted with 1.82 g. (0.01 moles) of 1-methyl-2-hydroxymethyl-4-nitro-5-cyanoimidazole as in the above procedure, there is obtained 1-methyl-2-(N-methylcarbamoyloxymethyl)-4-nitro-5-cyanoimidazole, m.p. 151° to 152°C.

EXAMPLE 9

1-Methyl-2-(N,N-dimethylcarbamoyloxymethyl)-4-nitro-5-cyanoimidazole 1.8 G. (0.01 moles) of 1-methyl-2-hydroxymethyl-4-nitro-5-cyanoimidazole and 2.14 g. (0.12 moles) of dimethylcarbamoyl chloride are combined in 15 ml. of pyridine and heated at 100°C. for 24 hours. The reaction mixture is evaporated to dryness, treated with 50 ml. of water and extracted with methylene chloride. The combined methylene chloride extracts are washed with water, dried, evaporated to dryness and the residue triturated with ether. The solid material is filtered and crystallized from isopropanol affording 1-methyl-2-(N,N-dimethylcarbamoyloxymethyl)-4-nitro-5-cyanoimidazole, m.p. 85° to 88°C.

When the following reactants are combined with 1.82 g. (0.01 moles) of 1-methyl-2-hydroxymethyl-4-nitro-5-cyanoimidazole, using the same procedure as above and employing basic solvents as pyridine or triethylamine, or a non-reactive solvent as methylene chloride, carbon tetrachloride, benzene, toluene and the like, containing at least a molecular equivalent of a base such as pyridine, or triethylamine, the following products are produced:

EXAMPLE 9

| Quantity | Reagent | Conditions | Product | m.p. (°C.) |
|---|---|---|---|---|
| 1.7 g. (0.011 m.) | phenoxycarbonyl chloride | 25°C. (16 hrs.) | 1-methyl-2-phenoxycarbonyl-oxymethyl-4-nitro-5-cyano-imidazole | 138–140°C. |
| 1.66 g. (0.0105 m.) | p-fluorobenzoyl chloride | 25°C. (1 hr.) | 1-methyl-2-(p-fluorobenzoyl-oxymethyl)-4-nitro-5-cyano-imidazole | 145–146°C. |

EXAMPLE 9-continued

| Quantity | Reagent | Conditions | Product | m.p. (°C.) |
| --- | --- | --- | --- | --- |
| 1.04 ml. (0.01 m.) | isobutyryl chloride | 25°C. (1 hr.) | 1-methyl-2-isobutyryloxy-methyl-4-nitro-5-cyano-imidazole | 58–61°C. |

When 0.196 g. (0.001 moles) of 1-methyl-2-(1-hydroxyethyl)-4-nitro-5-cyanoimidazole and 0.17 g. (0.0012 moles) of chlorosulfonylisocyanate are employed in the above procedure at 25°C. for 3 hours there is obtained 0.210 g. of 1-methyl-2-(1-carbamoyloxyethyl)-4-nitro-5-cyanoimidazole, m.p. 230° to 235°C. with decomposition.

EXAMPLE 10

1-Methyl-2-carboxy-4-nitro-5-cyanoimidazole-potassium salt 1.8 G. (0.01 moles) of 1-methyl-2-hydroxymethyl-4-nitro-5-cyanoimidazole is dissolved in 20 ml. of acetone and treated at 0°C. with a slurry of potassium permanganate (0.014 moles) in 15 ml. of water. The reaction mixture is stirred for 2 hours at 0°C. and overnight at room temperature. The reaction mixture is filtered and the filtrate evaporated in a high vacuum affording 1-methyl-2-carboxy-4-nitro-5-cyanoimidazole-potassium salt, m.p. 235° to 240°C.

EXAMPLE 11

1-Methyl-2-carbamoyl-4-nitro-5-cyanoimidazole 0.65 G. 1-methyl-2-carboxy-4-nitro-5-cyanoimidazole-potassium salt is dissolved in 25 ml. of benzene containing excess oxalylchloride and refluxed in benzene for ½ hour. The reaction mixture is evaporated to dryness and the residue slowly added to concentrated ammonium hydroxide at −10°C. The ammonium hydroxide solution is stirred at 0°C. for 15 minutes and filtered. The solid material is recrystallized from dimethylformamide/isopropanol affording 0.55 g. of 1-methyl-2-carbamoyl-4-nitro-5-cyanoimidazole, m.p. 265° to 267°C.

EXAMPLE 12

1-Methyl-2-formyl-4-nitro-5-cyanoimidazole 0.91 G. (0.05 moles) of 1-methyl-2-hydroxymethyl-4-nitro-5-cyanoimidazole and 2.66 g. of leadtetraacetate are combined in 35 ml. of benzene and refluxed for 12 hours. 0.3 G. of ethylene glycol is added to the reaction mixture to consume excess leadtetraacetate and the reaction mixture is filtered. The benzene solution is washed with water and sodium bicarbonate solution, dried and evaporated to dryness. The residue is recrystallized from isopropanol affording 1-methyl-2-formyl-4-nitro-5-cyanoimidazole, m.p. 130° to 133C.

EXAMPLE 13

1-Methyl-2-carboxaldehydethiosemicarbazone-4-nitro-5-cyanoimidazole 0.54 G. (0.003 moles) of 1-methyl-2-formyl-4-nitro-5-cyanoimidazole is dissolved in 2 ml. of dimethyl formamide and treated with 0.273 g. (0.003 moles) of thiosemicarbazide and 1 crystal of p-toluenesulfonic acid-hydrate. The reaction mixture is stirred for 12 hours at room temperature. 20 ml. of isopropanol is added and the mixture filtered affording a crystalline product which is dried overnight at a high vacuum at 100°C. affording 1-methyl-2-carboxaldehydethiosemicarbazone-4-nitro-5-cyanoimidazole, m.p. 230° to 235°C. with decomposition.

EXAMPLE 14

1-Methyl-2-carboxaldehydeoxime-4-nitro-5-cyanoimidazole 1.17 G. of 1-methyl-2-formyl-4-nitro-5-cyanoimidazole is dissolved in 20 ml. of ethanol and treated with 0.0055 moles of hydroxylamine hydrochloride. The reaction mixture is heated at reflux for 10 minutes, cooled and filtered, affording 1.0 g. of 1-methyl-2-carboxaldehydeoxime-4-nitro-5-cyanoimidazole, m.p. 245° to 247°C. with decomposition.

What is claimed is:

1. A composition useful for the prevention and treatment of coccidiosis which comprises an inert carrier vehicle and an active ingredient wherein said active ingredient is 1-methyl-2-(1-acetoxyethyl)-4-nitro-5-cyanoimidazole and said active ingredient is from about 0.00025% to 0.5% by weight of said composition.

2. An anticoccidial composition which comprises a solid edible carrier and the compound 1-methyl-2-acetoxymethyl-4-nitro-5-cyanoimidazole wherein said composition contains from about 2 to 25% by weight of said compound.

3. An anticoccidial composition which comprises a solid edible carrier and the compound 1-methyl-2-(1-acetoxyethyl)-4-nitro-5-cyanoimidazole wherein said composition contains from about 2 to 25%, by weight of said compound.

* * * * *